United States Patent

Albert et al.

[11] Patent Number: 5,405,968
[45] Date of Patent: Apr. 11, 1995

[54] POLYKETOMETHINE DYES

[75] Inventors: Bernhard Albert, Maxdorf; Knut Kessel, Mannheim; Hans-Dieter Martin, Wuerzburg; Stefan Silber, Krefeld, all of Germany

[73] Assignee: BASF Aktiengesellschaft, Ludwigshafen, Germany

[21] Appl. No.: 119,188

[22] PCT Filed: Mar. 28, 1992

[86] PCT No.: PCT/EP92/00693
§ 371 Date: Sep. 27, 1993
§ 102(e) Date: Sep. 27, 1993

[87] PCT Pub. No.: WO92/17549
PCT Pub. Date: Oct. 15, 1992

[30] Foreign Application Priority Data

Apr. 6, 1991 [DE] Germany .................. 41 11 159.1

[51] Int. Cl.⁶ .................. C07D 411/10; C07D 409/10; C07D 407/10; C07D 335/02
[52] U.S. Cl. .................................. 549/13; 549/14; 549/20; 549/22; 549/30; 549/39; 549/59; 549/60; 549/357; 549/370; 549/378; 549/414; 549/415; 549/448; 549/472
[58] Field of Search .............. 549/13, 14, 20, 30, 39, 59, 414, 448, 472, 60, 357, 370, 378, 415, 22

[56] References Cited

PUBLICATIONS

Chemical Abstracts 112(20) 189117p of JP 88-71515, 1989.

Primary Examiner—Alan L. Rotman
Assistant Examiner—D. Margaret M. Mach
Attorney, Agent, or Firm—Oblon, Spivak, McClelland, Maier, & Neustadt

[57] ABSTRACT

Methine dyes with a polyketo group I

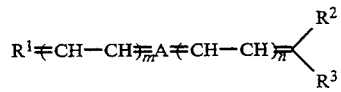

where

A is 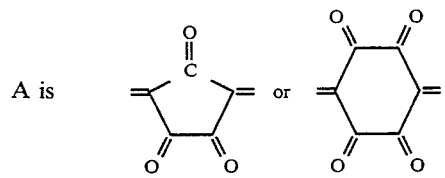

$R^1$ is a 5- or 6-membered cycloaliphatic radical which contains one or two hetero atoms from the group $-NR^4-$, $-O-$ and $-S-$ and which may be fused to an isoaromatic or heteroaromatic group, $R^2$ and $R^3$ are identical or different $C_1-C_{10}$-alkyl groups or together one of the radicals $R^1$, and m and n are identical or different integers from 0 to 3, are useful as drugs, for producing singlet oxygen, as sensitizers in electrophotographic layers and for photopolymerizations and as laser light sensitive dyes in optical recording media; also novel triketo- and tetraketomethine dyes.

1 Claim, No Drawings

POLYKETOMETHINE DYES

The present invention relates to novel polyketonmethine dyes of the general formula I

where

A is a group of the formula A1 or A2

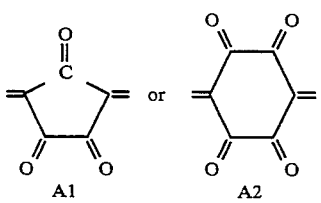

$R^1$ is a 5- or 6-membered cycloaliphatic radical which contains one or two hetero atoms from the group —NR4—, —O— and —S— and which may be fused to an isoaromatic or heteroaromatic group, where $R^4$ is a $C_5$-$C_7$-cycloalkyl group or a phenyl group which may carry halogen, $C_1$-$C_4$-alkyl or -alkoxy as substituents, or a $C_1$-$C_{20}$-alkyl group whose carbon chain may be interrupted by from one to five oxygen atoms in ether function and which may carry the following substituents: hydroxyl, phenyl, 1,3-dioxan-2-yl, 1,3-dioxolan-2-yl, —NHR$^5$, —NH-COR$^5$, —CONHR$^5$, —OCONHR$^5$, —N$^\oplus$(R$^5$)$_3$.An$^\ominus$, —SO$_3$H or —SO$_3^\ominus$Ka$^{108}$, where $R^5$ is one of the unsubstituted or hydroxyl- or phenyl-substituted alkyl radicals $R^4$ or phenyl and the radicals $R^5$ in the substituent —N$^\oplus$(R$^5$)$_3$ may be identical or different, An$^\ominus$ is the equivalent of an anion, and
Ka$^\oplus$ is the equivalent of a cation, $R^2$ and $R^3$ are identical or different $C_1$-$C_{10}$-alkyl groups or together one of the radicals $R^1$, provided that in the case of the group A1 radicals $R^1$ of the formulae

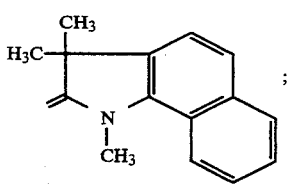

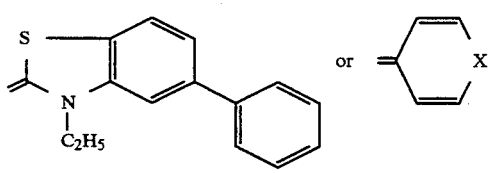

in which X is oxygen, sulfur, selenium, —N(CH$_3$)$_2$ or —N(C$_2$H$_5$)—CH$_2$—C$_6$H$_5$ and which may be substituted by alkyl, aryl or amino groups shall be excluded and in the case of the group A2 radicals $R^1$ of the formulae

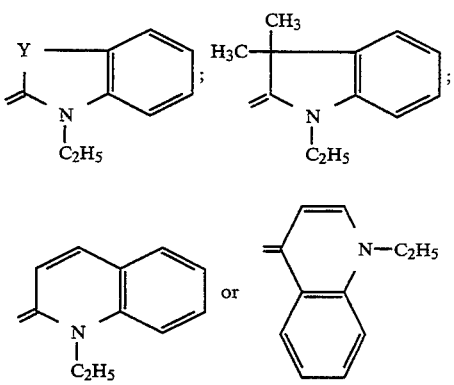

in which Y is oxygen or sulfur shall be excluded,
m and n are=identical or different integers from 0 to 3.

Dyes which absorb in the infrared region are of interest for many applications. They are frequently used as sensitizers for electrophotographic layers and for photopolymerizations and as laser light sensitive dyes in optical recording media.

If the dyes are additionally suitable for generating singlet oxygen, they are also of interest for use in photodynamic tumor therapy, which is based on the selective accumulation of dyes in cancer tissue and makes possible not only precise localization but also effective treatment even at an early stage of the tumor.

The irradiation of dye-enriched tumor tissue leads, probably via formation of singlet oxygen, to the selective destruction of the tumor tissue. Since the light transmissivity of body tissue rises steeply with increasing wavelength and for IR radiation of 800 nm is several powers of ten greater than for visible light, semiconductor lasers which emit light in the near IR region and dyes which show high absorption in that region are particularly suitable radiation sources for tumor therapy.

U.S. Pat. No. 5,002,812 and JP-A-242 288 (1989) describe the use of methine dyes having a cyclopentanetrione group based on benzofused indoline or on 3-ethylbenzothiazole and pyridine-, pyran- and thiopyrans in optical recording media.

U.S. Pat. No. 3,140,951 discloses methine dyes with a cyclohexanetetrone group based on 3-ethyl-benzoxazole and -benzothiazole, 1-ethyl-3,3-dimethyl-2-indole and 1-ethyl-2(1H)- and -4(1H)-quinoline, which, however, are used there as desensitizers for photographic emulsions.

It is an object of the present invention to find dyes which absorb in the infrared region and have favorable application properties.

We have found that this object is achieved by the polyketomethine dyes I.

The radical $R^1$ is a 5- or 6-membered cycloaliphatic radical which contains one or two hetero atoms from the group —NR$^4$—, —O— and —S— and which can be fused linearly or angularly with an isoaromatic or heteroaromatic group. Examples of preferred radicals $R^1$ are:

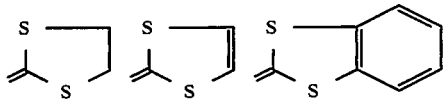

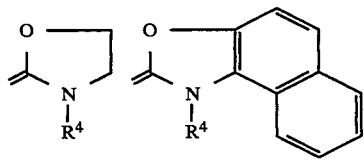

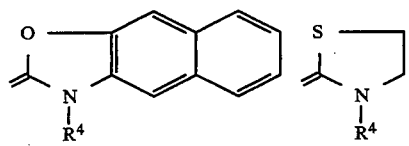

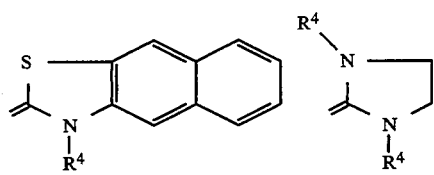

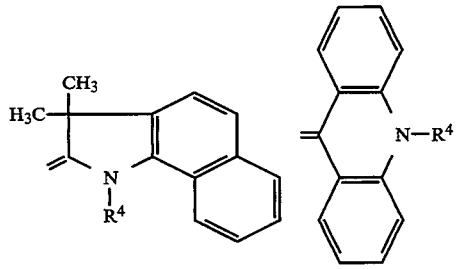

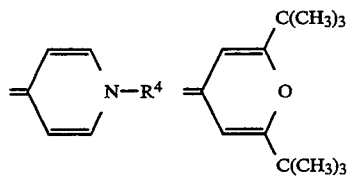

Examples of particularly preferred radicals $R^1$ are:

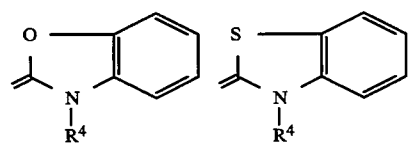

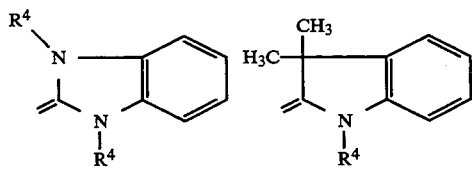

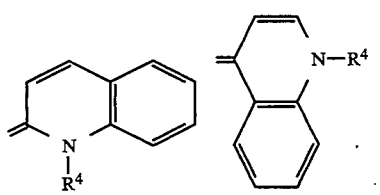

A very particularly preferred radical $R^1$ is

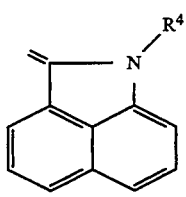

The fused benzene and naphthalene nuclei are preferably unsubstituted. However, they may also carry $C_1$–$C_5$-alkyl, -alkoxy, halogen, —$SO_3H$ or —$SO_3^{\ominus}$ $Ka^{\oplus}$ as substituents.

Suitable for use as radical $R^4$ are $C_1$–$C_{20}$-alkyl groups such as methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, nonyl, decyl, undecyl, dodecyl, tridecyl, tetradecyl, pentadecyl, hexadecyl, heptadecyl, octadecyl, nonadecyl and eicosyl and also branched radicals of this kind. Of these, the $C_1$–$C_{12}$-alkyl groups are preferred and the $C_1$–$C_6$-alkyl groups particularly preferred.

The carbon chains of these alkyl groups may be interrupted by oxygen atoms in ether function. In this case the $C_1$–$C_6$-alkyl groups generally contain one or two oxygen atoms in the chain, the $C_7$–$C_{12}$-alkyl groups up to three and the $C_{13}$–$C_{20}$-alkyl groups up to five. Examples are the following groups: preferably 2-methoxy-, 2-ethoxy-, 2-propoxy-, 2-isopropoxy- and 2-butoxyethyl, plus 2- and 3-methoxypropyl, 2- and 3-ethoxypropyl, 2- and 4-ethoxy-butyl, 2- and 4-isopropoxybutyl, 5-ethoxypentyl, 6-methoxyhexyl, 4-oxa-6-ethyldecyl, preferably 3,6-dioxaheptyl, 3,6-dioxaoctyl, 3,6-dioxadecyl, 3,6,9-trioxadecyl and 3,6,9-trioxaundecyl.

The alkyl radicals $R^4$ may additionally carry substituents such as hydroxyl, phenyl, 1,3-dioxan-2-yl and 1,3-dioxolan-2-yl. Examples are (Ph=phenyl):
—$(CH_2)_2$—OH, —$(CH_2)_3$—OH, —$CH_2$—CH(OH)—$CH_3$, —$(CH_2)_4$—OH, —$CH_2$—CH(OH)—$CH_2$—$CH_3$, —$(CH_2)_5$—OH, —$(CH_2)_6$—OH, —$(CH_2)_7$—OH, —$(CH_2)_8$—OH und —$(CH_2)_{11}$—OH; —$CH_2$—Ph, —$(CH_2)_2$—Ph, —CH(Ph)—$CH_3$ und —[$(CH_2)_2$—O]$_2$—$CH_2$—Ph;

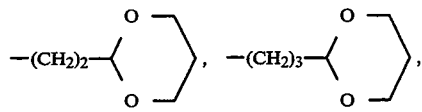

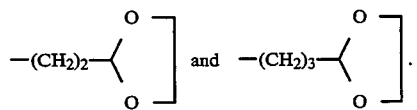

Further possible substituents for the alkyl radicals $R^4$ are those of the formulae —NH—$R^5$, —NH—CO—$R^5$, —CO—NH—R$^5$ and —O—CO—NH—R$^5$, which are preferably in the ω-position. Here R$^5$ is one of the unsubstituted or hydroxyl- or phenyl-substituted alkyl radicals R$^4$ whose carbon chain may be interrupted by oxygen atoms in ether function or phenyl. Examples of the radical R$^5$ are the appropriate groups listed above. Such substituted radicals R$^4$ are for example:

—(CH$_2$)$_2$—NH—CH$_3$, —(CH$_2$)$_3$—NH—C$_2$H$_5$, —CH(CH$_3$)—CH(CH$_3$)—NH—C$_2$H$_5$, —(CH$_2$)$_4$—NH—C$_3$H$_7$, —(CH$_2$)$_3$—NH—CH(CH$_3$)$_2$, —(CH$_2$)$_2$—NH—C$_4$H$_9$ and —(CH$_2$)$_2$—NH—Ph;

—CH(CH$_3$)—CH(CH$_3$)—NH—CO—CH$_3$, —(CH$_2$)$_4$—NH—CO—C$_2$H$_5$, —(CH$_2$)$_3$—NH—CO—C$_3$H$_7$, —(CH$_2$)$_2$—NH—CO—CH(CH$_3$)$_2$, —(CH$_2$)$_2$—NH—CO—C$_4$H$_9$, —(CH$_2$)$_2$—CO—NH—C(CH$_3$)$_3$ and —(CH$_2$)$_2$—NH—CO—Ph;

—CH(CH$_3$)—CH(CH$_3$)—CO—NH—CH$_3$, —(CH$_2$)$_4$—CO—NH—C$_2$H$_5$, —(CH$_2$)$_3$—CO—NH—C$_3$H$_7$, —(CH$_2$)$_2$—CO—NH—CH(CH$_3$)$_2$, —(CH$_2$)$_2$—CO—NH—C$_4$H$_9$, —(CH$_2$)$_2$—CO—NH—C(CH$_3$)$_3$ and —(CH$_2$)$_2$—CO—NH—Ph;

—(CH$_2$)$_4$—O—CO—NH—CH$_3$, —(CH$_2$)$_3$—O—CO—NH—C$_2$H$_5$, —(CH$_2$)$_3$—O—CO—NH—C$_3$H$_7$, —(CH$_2$)$_3$—O—CO—NH—CH(CH$_3$)$_2$, —(CH$_2$)$_3$—O—CO—NH—C$_4$H$_9$, —(CH$_2$)$_3$—O—CO—NH—C(CH$_3$)$_3$ and —(CH$_2$)$_2$—O—CO—NH—Ph.

Finally, substituents for the alkyl radicals R$^4$ may also be those of the formulae —N$^\oplus$(R$^5$)$_3$.An$^\ominus$, —SO$_3$H or —SO$_3^\ominus$.Ka$^\oplus$, likewise preferably in the ω-position. These radicals R$^5$ can be identical or different. Examples of these radicals R$^4$ are:

—(CH$_2$)$_2$—N$^\oplus$(C$_2$H$_5$)$_3$, —(CH$_2$)$_3$—N$^\oplus$(CH$_3$)$_3$, —(CH$_2$)$_3$—N$^\oplus$(C$_2$H$_5$)$_3$, —(CH$_2$)$_3$—N$^\oplus$(C$_4$H$_9$)$_3$, —(CH$_2$)$_4$—N$^\oplus$(C$_2$H$_5$)$_3$, —(CH$_2$)$_6$—N$^\oplus$(C$_2$H$_5$)$_3$, —(CH$_2$)$_{10}$—N$^\oplus$(C$_2$H$_5$)$_3$, —(CH$_2$)$_2$—N$^\oplus$(CH$_3$)(C$_2$H$_5$)$_2$ und —(CH$_2$)$_2$N$^\oplus$(CH$_3$)(C$_2$H$_5$)(C$_3$H$_7$);

—(CH$_2$)$_2$—SO$_3$H, —(CH$_2$)$_3$—SO$_3$H, —(CH$_2$)$_4$—SO$_3$H, —(CH$_2$)$_4$—SO$_3$H, —(CH$_2$)$_6$—SO$_3$H and —(CH$_2$)$_{10}$—SO$_3$H;

—(CH$_2$)$_2$—SO$_3^\ominus$, —(CH$_2$)$_3$—SO$_3^\ominus$, —(CH$_2$)$_4$—SO$_3^\ominus$, —(CH$_2$)$_6$—SO$_3^\ominus$ and —(CH$_2$)$_{10}$—SO$_3^\ominus$.

Suitable anions An$^\ominus$ can be anions of inorganic or organic acids. Particular preference is given for example to chloride, bromide and sulfate and also maleate, fumarate, tosylate and salicylate.

Suitable cations Ka$^\oplus$ can be alkali metal ions such as in particular Na$^\oplus$ and K$^\oplus$. Particular preference is given to trialkylammonium ions of the formula HN$^\oplus$(R$^5$)$_3$, for example those with the abovementioned groups —N$^\oplus$(R$^5$)$_3$.

Also suitable for use as radical R$^4$ are cyclopentyl, cyclohexyl, cycloheptyl and phenyl which may carry halogen, C$_1$-C$_4$-alkyl or -alkoxy as substituents, such as: 2-, 3- and 4-chlorophenyl, 2,4- and 2,6-dichlorophenyl, 2-, 3- and 4-bromophenyl, 2-, 3- and 4-methylphenyl, 2,4-dimethylphenyl, 2-, 3- and 4-methoxyphenyl and 2,4-dimethoxyphenyl.

Suitable for use as radicals R$^2$ and R$^3$ are the alkyl groups with up to 10 carbon atoms listed for the radical R$^4$ in which case R$^2$ and R$^3$ are preferably identical alkyl groups and are each particularly preferably methyl.

However, the radicals R$^2$ and R$^3$ may also be together one of the abovementioned radicals R$^1$. In this case not only asymmetrically but also symmetrically constructed methine dyes are possible, the latter being preferred.

The variables m and n are identical or different and can be 0, 1, 2 or 3. m is preferably 0 and particularly preferably 1. If the radicals R$^2$ and R$^3$ are each alkyl groups, n is preferably 0. If the radicals R$^2$ and R$^3$ together form a radical R$^1$, n preferably has the same value as m.

Methods for preparing methine dyes with a cyclohexanetetrone group are generally known; see for example US-A-3 140 951.

The polyketomethine dyes I according to the invention can be prepared in a similar manner, for example by condensing the group A compounds 1,2,4-cyclopentanetrione or 2,5-dihydroxy-p-benzoquinone with the

heterocyclic ammonium salts of the formula IIa

IIa

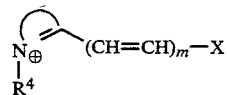

where X is a leaving group, which are described for example in Houben-Weyl, 4th edition, Volume V/1d, pages 239 to 240 (1972) or in J. Heterocyclic Chem. 22 (1985), 1727-1734.

If m is 0, X is preferably a methylmercapto group, while if m ≧ 1 the preferred leaving group is acetanilido.

A further way of introducing the group

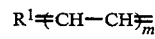

is to use the corresponding aldehydes of the formula IIb

IIb

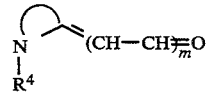

in the condensation.

The compounds IIa and IIb are obtainable by reacting the respective unsubstituted nitrogen heterocycles with a compound R$^4$-Y where Y is for example chlorine, bromine, iodine, —O—SO$_2$—Ph—4—CH$_3$, —O—SO$_2$—CH$_3$ or —O—SO$_2$—CF$_3$.

If m is 0 it is also possible to use the activated dimeric heterocycles, for example those of the formulae

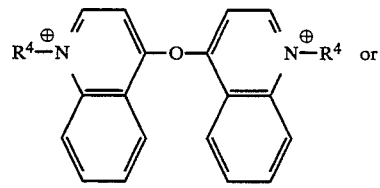 or

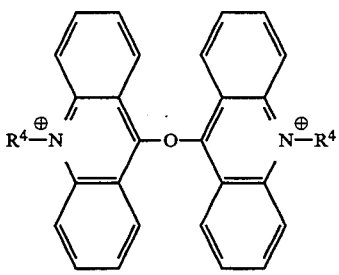

Vice versa, the condensation can also be carried out similarly to US-A-3 140 951 or Houben-Weyl, 4th edition, Volume V/1d, pages 239 to 290 (1972), with 1,2,4-cyclopentanetrione or 1,2,4,5-cyclohexanetetrone which is in each case disubstituted by anilinomthylene (leaving group —NH—Ph), and the 2-methylated heterocyclic ammonium salts (m=1).

To form the polymethine chain (m=2 or 3) the 2-methylated heterocyclic salts can be reacted, for example as described in Houben-Weyl, 4th edition., Volume V/1d, pages 268 to 274 (1972), with, for example, compounds of the formula

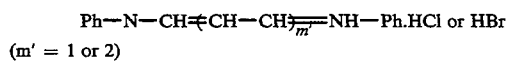

(m' = 1 or 2)

in acetic anhydride to form a hemicyanine of the formula

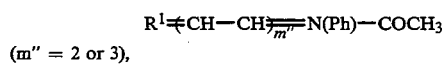

(m'' = 2 or 3), which can then be used for further condensation with group A.

To prepare the similarly novel asymmetrical polyketomethine dyes of the formula I where $R^2$ and $R^3$ are each alkyl, the starting materials used for the condensation are 5,5- and 6,6-dialkylated 1,2,4-cyclopentanetriones and 2,5-dihydroxy-p-benzoquinones respectively.

The condensation is preferably carried out in a solvent, such as diethyl ether, tetrahydrofuran, trichloroethylene, 1,1,1-trichloroethane, methylene chloride, chloroform, methanol, ethanol, propanol, isopropanol, butanol, glacial acetic acid, propionic acid or acetonitrile, preferably in the presence of a catalyst, such as ammonium acetate, piperidine or pyridine or acetates thereof, at a temperature between 20° C. and the boiling point of the solvent used.

Preference is given to using tertiary amines such as tripropylamine, tributylamine and in particular triethylamine, picolines, lutidines and in particular pyridine or mixtures thereof as solvents, since in these cases no separate catalyst need be added.

A further way of preparing methine dyes I with dialkylation in the 6-position of the cyclohexanetetrone consists in reacting the 5,5-dialkyl-1,3-cyclohexanedione with a heterocyclic ammonium salt having a leaving group and then selectively oxidizing the resulting condensation product with selenium dioxide in a solvent such as glacial acetic acid to give the corresponding tetraketo compound.

The polyketomethine dyes I of the invention show in some cases high absorption in the infrared region. They are highly suitable for producing singlet oxygen and can therefore be used in photodynamic tumor therapy, for example.

They are also suitable for use as sensitizers in electrophotographic recording materials as are described for example in EP-A-150 419. Suitable monolayered systems of this type preferably support on a conductive base material a layer comprising from 45 to 75 parts by weight of a binder, from 30 to 60 parts by weight of a charge carrier transporter compound, optionally up to 25 parts by weight of a further, essentially inactive binder and from 0.05 to 0.8 part by weight of the sensitizer which generates charge carriers on actinic irradiation. This layer is advantageously applied to the purified conductive base material from an approximately 6% strength by weight solution in a suitable organic solvent in such as way as to leave, after the solvent has been flashed off, a dry layer in a thickness, depending on the intended use, from about 0.8 to 40 μm, especially in the case of electrophotographic printing plates from 0.8 to 6 μm. Further details on the formation of these systems can be found in EP-A-150 419.

Furthermore, the dyes I are suitable for use as sensitizers for photopolymerizations, for example for the curing of surface coatings. Finally, they can be used, as described in US-A-4 904 566 for azulene squaric acid dyes, as laser light sensitive dyes in optical recording media.

EXAMPLES a) Preparation of polyketomethine dyes I a1) Preparation of symmetrical triketomethine dyes Ia'

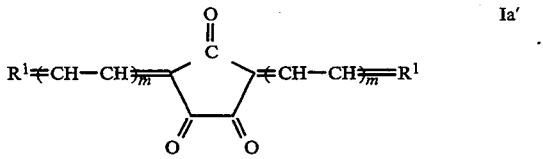

Example 1

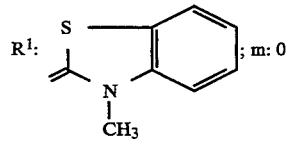

A mixture of 1.61 g (5 mmol) of 3-methyl-2-methylmercaptobenzothiazolium iodide, 0.28 g (2.5 mmol) of 1,2,4-cyclopentanetrione and 2 ml of freshly distilled triethylamine in 20 ml of ethanol was refluxed for 30 min.

The precipitate produced on quenching was separated off, washed in succession with methanol, ethyl acetate and ether and then recrystallized twice from dimethylformamide.

The 3,5-di-(3-methyl-2-benzothiazolinylidene)-1,2,4-cyclopentanetrione was obtained in a yield of 0.45 g (42% of theory):

melting point:>250° C.; $\lambda_{max}$ =467 nm ($CH_2Cl_2$).

Example 2

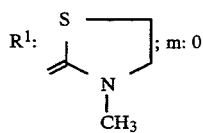

R¹: [structure]; m: 0

The reaction with 1.37 g (5 mmol) of 3-methyl-2-methylmercaptothiazolinium iodide was carried out as described in Example 1. The product was recrystallized from acetonitrile.

The 3,5-di-(3-methyl-2-thiazolinylidene)-1,2,4-cyclopentanetrione was obtained in a yield of 0.35 g (45% of theory):

melting point: >250° C.; $\lambda_{max}$=399 nm (CH$_2$Cl$_2$).

Example 3

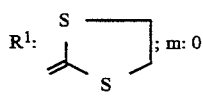

R¹: [structure]; m: 0

A mixture of 1.31 g (5 mmol) of 2-methylmercapto-1,3-dithiolanium methosulfate, 0.28 g (2.5 mmol) of 1,2,4-cyclopentanetrione and 2 ml of freshly distilled triethylamine in 20 ml of pyridine was refluxed for 45 min.

The precipitate produced on cooling was separated off, washed in succession with methanol and ethyl acetate and recrystallized from dimethylformamide.

The 3,5-di(2-dithiolanylidene)-1,2,4-cyclopentanetrione was obtained in a yield of 0.48 g (61% of theory):

melting point: >250° C.; $\lambda_{max}$=446 nm (dimethylformamide).

Examples 4 TO 7

The triketomethine dyes Ia' shown in Table 1 were prepared analogously to Example 3 by reacting 1,2,4-cyclopentanetrione with 2-methylmercapto-1,3-dithiolium methosulfate (Example 4) or with the corresponding heterocyclic ammonium iodide with an acetanilidovinyl substituent in the 2-position (Examples 5 to 7).

TABLE 1

$$R^1\!\!=\!\!CH\!-\!CH)_{\overline{m}}\!\!\diagup\!\!\!\overset{\overset{O}{\|}}{\underset{\underset{O}{\|}}{C}}\!\!\!\diagdown\!(\!CH\!-\!CH)_{\overline{m}}\!\!=\!\!R^1 \quad \text{Ia'}$$

| Ex. | R¹ | m | Yield in g/% | mp. [°C.] | $\lambda_{max}$ [nm] |
|---|---|---|---|---|---|
| 4 | [S-S thiolanylidene] | 0 | 0,62/79* | >250 | 527 (CH$_2$Cl$_2$) |
| 5 | [S-N(C$_2$H$_5$) thiazolinylidene] | 1 | 0,84/86 | >250 | 597 (dimethylformamide) |
| 6 | [S-N(C$_2$H$_5$) benzothiazolinylidene] | 1 | 0,93/76 | >250 | 678 (dimethylformamide) |
| 7 | [O-N(C$_2$H$_5$) benzoxazolinylidene] | 1 | 0,82/72 | >250 | 618 (dimethylformamide) |

*Recrystallized from N,N-dimethylacetamide

Example 8

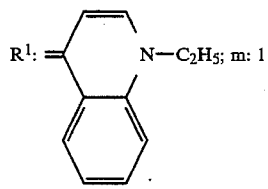

R¹: [quinolinylidene structure] N—C$_2$H$_5$; m: 1

A mixture of 1.52 g (5mmol) of 1-ethyl-4-methylquinolinium iodide, 0.80 g (2.5 mmol) of 3,5-dianilinomethylene-1,2,4-cyclopentanetrione and 1 ml of freshly distilled triethylamine in 20 ml of acetonitrile was stirred in the dark at room temperature for 3 days.

The resulting precipitate was separated off, washed with methanol and recrystallized from N,N-dimethylformamide.

The 3,5-di((1-ethyl-4(1H)quinolinylidene)-ethylidene)-1,2,4-cyclopentanetrione was obtained in a yield of 0.68 g (57% of theory):

melting point: >250° C.; $\lambda_{max}$=816 nm (dimethyl sulfoxide).

Examples 9 TO 13

The triketomethine dyes Ia" listed in Table 2 were prepared analogously to Example 8 by reacting 3,5-dianilinomethylene-1,2,4-cyclopentanetrione with the corresponding heterocyclic ammonium iodide and obtained in similar yields.

TABLE 2

$$R^1=CH-CH\overset{\overset{O}{\underset{\underset{O}{\|}}{\|}}}{C}=CH-CH=R^1 \quad \text{Ia''}$$

| Ex. | R¹ | λ_max [nm] |
|---|---|---|
| 9 | 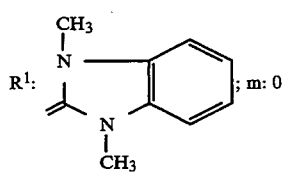 (N-C₂H₅ quinoline-type) | 731 (dimethyl sulfoxide) |
| 10 | CH₃, H₃C— indoline with N-C₂H₅ | 662 (dimethyl sulfoxide) |
| 11 | CH₃, H₃C— indoline with N-CH₃ | 652 (CH₂Cl₂) |
| 12 | CH₃, H₃C— 5-Cl indoline with N-C₂H₅ | 655 (CH₂Cl₂) |
| 13 | CH₃, H₃C— 5-Cl indoline with N-CH(CH₃)₂ | 621 (dimethyl sulfoxide) |

Example 14

$$R^1: \text{(1,3-dimethylbenzimidazolinylidene)}; \ m: 0$$

A mixture of 1.46 g (5 mmol) of 1,3-dimethyl-2-methylmercaptobenzimidazolium perchlorate, 0.28 g (2.5 mmol) of 1,2,4-cyclopentanetrione and 2 ml of freshly distilled triethylamine in 20 ml of acetonitrile was refluxed for 2h.

The precipitate formed on cooling was separated off, washed with water and recrystallized from N,N-dimethylacetamide.

The 3,5-bis ( 1,3-dimethyl-2-benzimidazolinylidene)-1,2,4-cyclopentanetrione was obtained in a yield of 0.23 g (23% of theory):

melting point:>250° C.; λ_max=362 nm (CH₂Cl₂).

Example 15

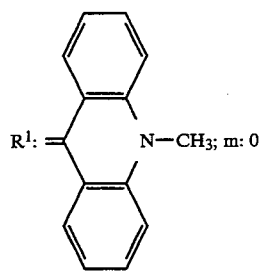

$$R^1: \text{(10-methyl-9-acridanylidene)}; \ m: 0$$

A solution of 1.40 g (2 mmol) of 9,9'-oxybis(10-methylacridinium) bis (trifluoromethanesulfonate ) in 20 ml of acetonitrile was added dropwise at room temperature to a mixture of 0.11 g (1 mmol) of 1,2,4-cyclopentanetrione, 20 ml of acetonitrile and 2 ml of freshly distilled triethylamine.

The resulting precipitate was separated off and washed with a large amount of methylene chloride.

The 3,5-bis(10-methyl-9-acridanylidene)-1,2,4-cyclopentanetrione was obtained in a yield of 0.42 g (71% of theory):

melting point:>250° C.; λ_max =788 nm (CH₂Cl₂).

a2) Preparation of symmetrical tetraketomethine dyes Ib'

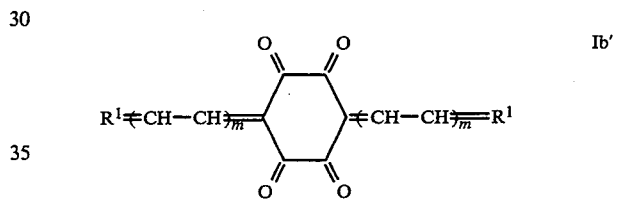

Example 16

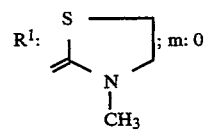

A mixture of 4 g ( 14.5 mmol ) of 3-methyl-2-methylmercaptothiazolinium iodide, 1 g ( 7.1 mol ) of 2,5-dihydroxy-p-benzoquinone and 2.5 ml of freshly distilled triethylamine in 40 ml of pyridine was refluxed for 10 min.

The precipitate formed on cooling was separated off and recrystallized from dimethylformamide.

The 3,6-di- (3-methyl-2-thiazolinylidene ) -1,2,4,5-cyclohexanetetrone was obtained in a yield of 1.09 g (45% of theory):

melting point:>300° C.; λ_max=372 nm (dimethyl sulfoxide).

Example 17

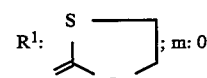

A mixture of 2.62 g (10 mmol) of 2-methylmercapto-1,3-dithiolanium methosulfate, 0.70 g (5mmol) of 2,5- dihydroxy-p-benzoquinone and 2 ml of freshly distilled triethylamine in 30 ml of pyridine was refluxed for 15 min.

The precipitate formed on quenching was separated off, washed in succession with methanol and acetone and then dissolved in hot m-cresol. After filtration, the still hot solution was poured into an excess of cold methanol to precipitate the target product.

The 3,6-bis(1,3-dithiolan-2-ylidene)-1,2,4,5-cyclohexanetetrone was obtained in a yield of 1.02 g (59% of theory):

melting point:>300° C.; $\lambda_{max}$=415 nm (dimethyl sulfoxide).

Example 18

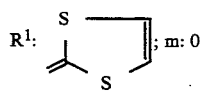

The reaction with 2.60 g (10 mmol) of 2-methyl-mercapto-1,3-dithiolium methosulfate and the isolation of the product were each carried out analogously to Example 17.

The 3,6-bis (1,3-dithiol-2-ylidene)-1,2,4,5-cyclohexanetetrone was obtained in a yield of 1.46 g (86% of theory):

melting point: 300° C.; $\lambda_{max}$=466 nm (dimethyl sulfoxide).

Example 19

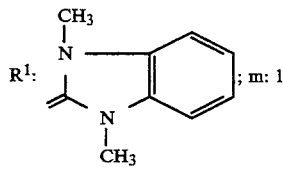

A mixture of 2.88 g (10 mmol) of 1,2,3-trimethyl-benzimidazolium iodide and 0.69 g ( 2 mmol ) of 3,6-dianilinomethylene-1,2,4,5-cyclohexanetetrone in 25 ml of N,N-dimethylformamide was refluxed for 2 min.

The precipitate formed on quenching was separated off, repeatedly washed with methanol and recrystallized from N,N-dimethylacetamide.

The 3,6-bis (2-(1,3-dimethyl-2-benzimidazolinylidene)ethylidene) -1,2,4,5-cyclohexanetetrone was obtained in a yield of 0.43 g (45% of theory):
melting point:>280° C.; $\lambda_{max}$=477 nm (CH$_2$Cl$_2$).

Example 20

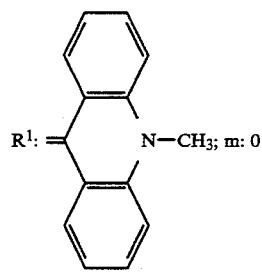

A solution of 1.40 g (5 mmol) of 9,9'-oxybis(10-methylacridinium) bis(trifluoromethanesulfonate) in 20 ml of acetonitrile was added dropwise at room temperature to a mixture of 0.14 g (1 mmol) of 2,5-dihydroxy-p-benzoquinone, 20 ml of acetonitrile and 2 ml of freshly distilled triethylamine.

The precipitate formed was separated off and washed with a large amount of methylene chloride.

The 3,6-bis(10-methyl-9-acridanylidene)-1,2,4,5-cyclohexanetetrone was obtained in a yield of 0.38 g (61% of theory):

melting point:>250° C.; $\lambda_{max}$=693 nm (CH$_2$Cl$_2$).

Example 21

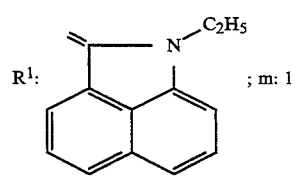

A mixture of 2.28 g (8.6 mmol) of 2-ethyl-1-methylbenzo[c,d]indolium iodide, 1.00 g (2.9 mmol) of 3,6-dianilinomethylene-1,2,4,5-cyclohexanetetrone and 1 ml of freshly distilled triethylamine in 30 ml of pyridine was refluxed for 10 min.

The precipitate formed on quenching was separated off, washed in succession with methanol and diethyl ether and then dried.

The 3,6-di((2-ethylbenzo[c,d]indolinylidene)-ethylidene)-1,2,4,5-cyclohexanetetrone were obtained in a yield of 1.4 g:

$\lambda_{max}$=751 nm (CH$_2$Cl$_2$).

Examples 22 TO 28

The tetraketomethine dyes Ib″ listed in Table 3 were prepared analogously to Example 21 by reacting 3,6-dianilinomethylene-1,2,4,5-cyclohexanetetrone with the corresponding heterocyclic ammonium iodide.

TABLE 3

| | Ib″ |
|---|---|
| $R^1$=CH—CH= ... =CH—CH=$R^1$ | |

| Ex. | $R^1$ | $\lambda_{max}$ [nm] |
|---|---|---|
| 22 | 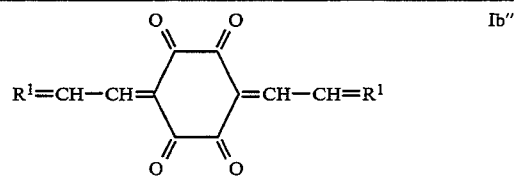 N—C$_{12}$H$_{25}$(n) | 725 (CH$_2$Cl$_2$) |
| 23 | N—(CH$_2$)$_{11}$—OH | 723 (CH$_2$Cl$_2$) |

TABLE 3-continued

Ib''

R¹=CH—CH=⟨cyclohexanetetrone⟩=CH—CH=R¹

| Ex. | R¹ | λ_max [nm] |
|---|---|---|
| 24 | =CH-quinoline-N—[(CH₂)₂—O]₂—C₂H₅ | 732 (CH₂Cl₂) |
| 25 | =CH-quinoline-N—(CH₂)₃—dioxane | 731 (CH₂Cl₂) |
| 26 | =CH-pyran with C(CH₃)₃ groups | 623 (CH₂Cl₂) |
| 27 | indoline with CH₃, H₃C, N-CH₃ | 603 (CH₂Cl₂) |
| 28 | indoline with CH₃, H₃C, N-(CH₂)₂—O—CO—NH—Ph | 611 (CH₂Cl₂) |
| 29 | thiazoline with n-C₈H₁₇ | 634 (dimethylformamide) |

Example 30

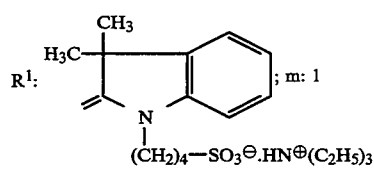

A mixture of 1.92 g (6.5 mmol) of 2,3,3-trimethylindolinium-1-(butane-4-sulfonate), 1.00 g (2.9 mmol) of dianilinomethylene-1,2,4,5-cyclohexanetetrone and 2 ml of freshly distilled triethylamine in 30 ml of pyridine was refluxed for 10 min.

After cooling, the precipitate formed was separated off, washed with ethyl acetate and dried.

Yield: 0.25 g; melting point: 265° C.

a3) Preparation of asymmetrical tetraketomethine dyes Ic

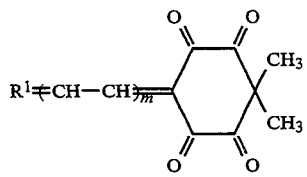

Example 31

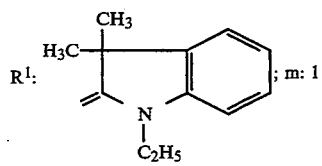

A mixture of 0.32 g (1 mmol) of 1-ethyl-2,3,3-trimethylindolinium iodide, 0.27 g (1 mmol.) of 3-anilinomethylene-6,6-dimethyl-1,2,4,5-cyclohexanetetrone and 0.5 ml of freshly distilled triethylamine in 10–15 ml of acetonitrile was stirred at an oil bath temperature of 50° C. for 3 days.

The precipitate formed was separated off, washed with water, dried, and recrystallized from dioxane.

The 6,6-dimethyl-3-(2-(1-ethyl-3,3-dimethyl-2-indolinylidene)ethylidene)-1,2,4,5-cyclohexanetetrone were obtained in a yield of 0.19 g (52% of theory): melting point:>250° C.; λ_max=507 nm (CH₂Cl₂).

Examples 32 TO 36

The tetraketomethine dyes Ic listed in Table 4 were prepared analogously to Example 31 by reacting 3-anilinomethylene-6,6-dimethyl-1,2,4,5-cyclohexanetetrone with the corresponding heterocyclic ammonium iodide.

TABLE 4

Ic

R¹=CH—CH=⟨6,6-dimethyl-cyclohexanetetrone⟩

| Ex. | R¹ | Yield in g/% | mp. [°C.] | λ_max [nm] |
|---|---|---|---|---|
| 32 | benzothiazoline with N-C₂H₅ | 0,23/66 | >250 | 504 (dimethylformamide) |
| 33 | =CH-N-CH₃ heterocycle | 0,23/81 | >250 | 483 (CH₂Cl₂) |

TABLE 4-continued $$R^1=CH-CH= \begin{array}{c} \text{(cyclohexanetetrone with } CH_3, CH_3) \end{array} \quad Ic$$

| Ex. | R¹ | Yield in g/% | mp. [°C.] | $\lambda_{max}$ [nm] |
|---|---|---|---|---|
| 34 | (S-CH₂-CH₂-N-C₂H₅ benzothiazoline) | 0,09/29* | >250 | 443 (dimethylformamide) |
| 35 | (quinoline derivative, N-C₂H₅) | 0,31/89** | >250 | 520 (Cl₂Cl₂) |
| 36 | (quinoline derivative, N—C₂H₅) | 0,33/95** | >250 | 539 (CH₂Cl₂) |

*Recrystallized from ethanol
**Recrystallized from N,N-dimethylformamide

Example 37

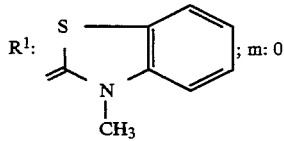

$R^1$: (5,5-dimethyl-benzothiazolinylidene structure); m: 0

A mixture of 8.62 g (0.03 mmol) of 5,5-dimethyl-2-(3-methylbenzothiazolinylidene)-1,3-cyclohexanedione, obtained by 1:1 condensation of 5,5-dimethyl-1,3-cyclohexanedione with 3-methyl-2-methylmercaptobenzothiazolium iodide in boiling 2-propanol, and 7.77 g (0.07 mol) of selenium dioxide in 50 ml of glacial acetic acid was stirred at an oil bath temperature of 130° C. for 5 h.

The resulting elemental selenium was separated off, and the glacial acetic acid was removed in a rotary evaporator. The residue was taken up in methylene chloride and filtered at the boil to remove insolubles. The remaining solution was cooled down to −15° C. to bring down crystals of the target product.

The 6,6-dimethyl-3-(3-methylbenzothiazolinylidene)-1,2,4,5-cyclohexanetetrone was obtained in a yield of 4.42 g (47% of theory):

melting point:>250° C.; $\lambda_{max}$=389 nm (dimethyl sulfoxide).

b) Use Examples b1) Production of singlet oxygen

The dyes I listed in Tables 5 and 6 and prepared analogously to a) were dissolved in the stated solvent and stimulated with a dye laser in the absorption bands.

The singlet oxygen formed was determined by time-resolved measurement of the phosphorescence at 1270 nm using a germanium diode cooled with liquid nitrogen (for the method see J. Amer. Chem. Soc. 111 (1989), 2909–2914); the calibrating substance used was 1,5-diaminoanthraquinone.

TABLE 5

$$R^1 \!\!\!=\!\!\! CH\!\!-\!\!CH)_{\overline{m}} \!\!\!\!\begin{array}{c}\text{(cyclopentanone ring with C=O)}\end{array}\!\!\!\! \!=\!\!CH\!\!-\!\!CH)_{\overline{m}}\!\!=\!\!R^1$$

| Ex. | R¹ | m | Singlet oxygen yield [%] | λ [nm] |
|---|---|---|---|---|
| 1A | (S—CH₂—CH₂—S benzothiazoline) | 0 | 20,1 | 446 (dimethylformamide) |
| 2A | 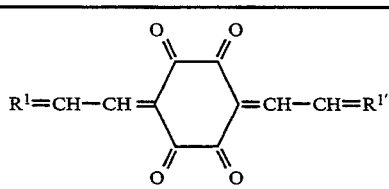 | 1 | 1,1 | 670 (methanol) |

TABLE 6

$$R^1=CH-CH= \begin{array}{c}\text{(cyclohexanetetrone)}\end{array} =CH-CH=R^{1'}$$

| Ex. | R¹ | R¹' | Singlet oxygen yield [%] | λ [nm] |
|---|---|---|---|---|
| 3A | (CH₃, H₃C indoline N-CH₃) | R¹ | 8,3 | 590 (CH₂Cl₂) |

TABLE 6-continued $$R^1=CH-CH=\underset{\underset{O\quad O}{\|\quad\|}}{\overset{\overset{O\quad O}{\|\quad\|}}{\bigcirc}}=CH-CH=R^{1'}$$

| Ex. | R¹ | R¹' | Singlet oxygen yield [%] | λ [nm] |
|---|---|---|---|---|
| 4A | 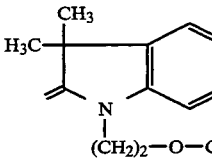 | R¹ | 4,7 | 590 (ethanol) |
| 5A | 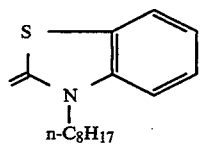 | R¹ | 4,4 | 634 (dimethylformamide) |
| 6A | 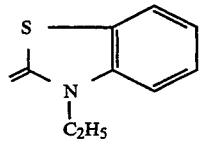 | 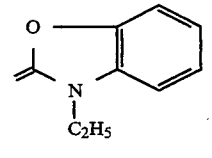 | 1,9 | 462 (dimethylformamide) |
| 7A | 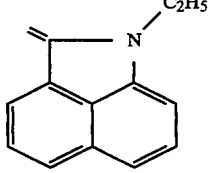 | R¹ | 2,6 | 670 ($CH_2Cl_2$) |
| 8A | 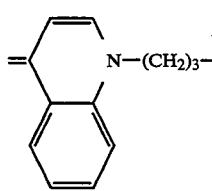 | R¹ | 6,1 | 670 ($CH_2Cl_2$) |
| 9A | 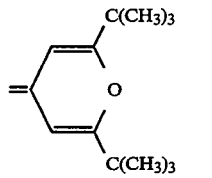 | R¹ | 9,8 | 600 (toluene) | b2) Preparation of photoconductor layers

The dyes I listed in Table 7 and prepared analogously to a) were used for preparing photoconductor layers.

To this end a 10% strength by weight solution of a mixture of 1% by weight of dye I as sensitizer, 27% by weight of 2-(4'-ethylphenylaminophenyl)-6-methoxybenzo-1,2,3-triazole and 18% by weight of 2,5-bis-4,4-diethylaminophenyl-1,2,3-oxadiazole as charge carrier transporter compounds and 54% by weight of a copolymer of 55% by weight of styrene, 25% by weight of acrylic acid, 15% by weight of maleic anhydride and 5% by weight of vinyl acetate (K value 36) as binder was stirred in 1:1 acetone/tetrahydrofuran at room temperature for 3 h.

After filtration, the solution was applied with a doctor blade to a finely brushed, 105 μm thick sheet of aluminum in such a way as to produce, after solvent flashoff and drying (15 min at 80° C.), a coating with a dry film thickness of 4.0±0.1 μm.

The plate thus coated was stored in the dark for 25 h and charged up with a high-voltage corona to the surface potential maximum. Then the loss of potential in the course of 20 sec in the dark (dark conductivity) and the photopotential decay induced by irradiation with the white light of a 100 W XDO xenon high-pressure lamp at a distance of 45 cm in the course of 10 sec were measured.

TABLE 7

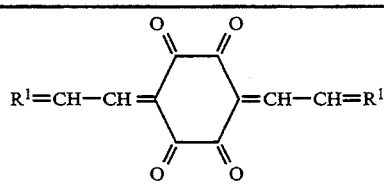

| Ex. | R¹ | Potential loss in the dark [%] | Photopotential decay [%] |
|---|---|---|---|
| 10A | ![C(CH₃)₃, O, C(CH₃)₃ structure] | 32,0 | 95,7 |
| 11A | ![N-C₂H₅ naphthalene structure] | 21,9 | 73,8 |
| 12A | ![N—[(CH₂)₂—O]₂—C₂H₅ structure] | 13,4 | 81,1 |

We claim:
1. Polyketomethine dyes of the formula I

I where
A is a group of the formula A1 or A2

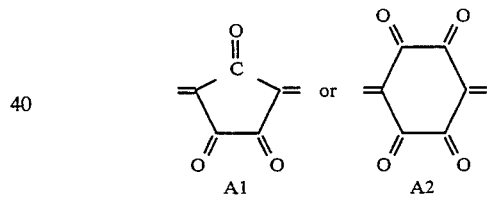

$R^1$ is 5- or 6-membered cycloaliphatic radical which contains one or two heteroatoms from the group —O— and —S— and which may be fused to an isoaromatic group, $R^2$ and $R^3$ are identical or different $C_1$-$C_{10}$-alkyl groups or together one of the radicals $R^1$, provided that in the case of the group A1 radicals R1 of the formula

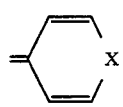

in which X is oxygen, sulfur, selenium, —$N(CH_3)_2$ or —$N(C_2H_5)$—$CH_2$ and which may be substituted by alkyl, aryl or amino groups shall be excluded; and m and n are identical or different integers from 0 to 3.

* * * * *